United States Patent [19]

Arndt et al.

[11] 4,257,803
[45] Mar. 24, 1981

[54] DIURETHANES AND METHODS FOR THEIR USE IN HERBICIDAL COMPOSITIONS

[75] Inventors: Friedrich Arndt; Gerhard Boroschewski, both of Berlin, Fed. Rep. of Germany

[73] Assignee: Schering Aktiengesellschaft, Berlin and Bergkamen, Fed. Rep. of Germany

[21] Appl. No.: 81,320

[22] Filed: Oct. 3, 1979

[30] Foreign Application Priority Data

Oct. 4, 1978 [DE] Fed. Rep. of Germany ....... 2843691

[51] Int. Cl.³ .................. C07C 121/50; C07C 155/02
[52] U.S. Cl. ..................................... 71/100; 71/111; 260/465 D; 260/455 A
[58] Field of Search ............. 260/465 D, 455 A; 71/100, 111

[56] References Cited

U.S. PATENT DOCUMENTS 3,036,112   5/1962   Lynn .................................. 260/465 D
3,551,477  12/1970   Koenig et al. ................... 260/465 D

*Primary Examiner*—Henry R. Jiles
*Assistant Examiner*—Robert C. Whittenbaugh
*Attorney, Agent, or Firm*—Michael J. Striker

[57] ABSTRACT

Novel diurethanes of the general formula

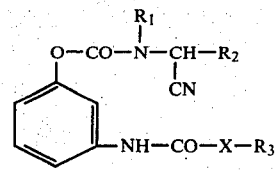

are described, in which $R_1$ is hydrogen, $C_1$–$C_4$ alkyl or $C_2$–$C_4$ alkenyl, $R_2$ is phenyl, methylphenyl, methoxyphenyl, chlorophenyl, dichlorophenyl, cyclohexyl, benzyl or phenylethyl, $R_3$ is $C_1$–$C_4$ alkyl, $C_2$–$C_4$ alkenyl, $C_2$–$C_4$ alkinyl, chloro-$C_1$–$C_4$ alkyl, chloro-$C_2$14 $C_4$ alkenyl, or chloro-$C_2$–$C_4$ alkinyl and X is oxygen or sulfur. Compositions containing at least one of the compounds of the general formula exhibit exceptional selective herbicidal properties.

110 Claims, No Drawings

DIURETHANES AND METHODS FOR THEIR USE IN HERBICIDAL COMPOSITIONS

The invention concerns novel diurethanes, methods for their preparation as well as a selective herbicidal composition containing at least one of these compounds.

Herbicidal diurethanes are already known (German published Pat. No. 1,567,151, U.S. Pat. No. 3,692,820). A very good selectivity is shown by these compounds with respect to beets, but in other cultures, such as for example cotton, bush beans, peanuts, potatoes, rice and alfalfa, this selectivity is not shown.

It is therefore an object of the invention to provide new active agents with increased selective herbicidal properties.

The object is achieved according to the invention through a composition which contains at least one compound of the general formula

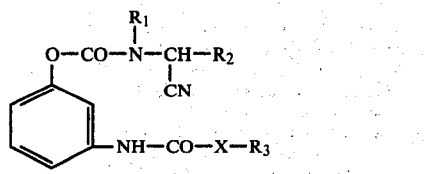

in which $R_1$ is hydrogen, $C_1$–$C_4$ alkyl or $C_2$–$C_4$ alkenyl, $R_2$ is phenyl, methylphenyl, methoxyphenyl, chlorophenyl, dichlorophenyl, cyclohexyl, benzyl or phenylethyl, $R_3$ is $C_1$–$C_4$ alkyl, $C_2$–$C_4$ alkenyl, $C_2$–$C_4$ alkinyl, chloro-$C_1$–$C_4$ alkyl, chloro-$C_1$–$C_4$ alkenyl, or chloro-$C_2$–$C_4$ alkinyl, and X is oxygen or sulfur.

The inventive diurethanes exhibit a very broad spectrum of activity with full compatibility towards many agricultural culture plants and are therefore a technical advance over the known urethanes in this respect.

The inventive diurethanes are seen to have a broad leaf herbicidal activity and thus can be used for combatting dicotyledonous weeds.

In post emergence treatments, weeds such as for example Amaranthus, Stellaria, Matricaria, Lamium, Centaurea, Ipomea, Solanum, Brassica, Senecio, Chrysanthemum, Polygonum and others are combatted.

To combat the weeds as a rule amounts of between about 1 kg to 5 kg/ha are applied. At this rate of application, the active agents are selective in useful plant cultures such as cotton, bush beans, peanuts, potatoes, rice, sugar beets and alfalfa.

The inventive compounds may be used alone, in mixtures with one another or in mixtures with other active agents. If desired, other agents such as defoliants, plant protection agents or pest control agents can be added, according to the desired purpose.

Insofar as a broadening of the activity spectrum is desired, other herbicides can also be added. For example, suitable mixture partners can be selected from such active agent types as triazines, aminotriazoles, anilides, diazines, uracils, aliphatic carboxylic acids and aryloxycarboxylic acids and hydrazides, amides, nitriles and esters of such carboxylic acids, carbamide and thiocarbamide esters, ureas, 2,3,6-trichlorobenzyloxypropanil, thiocyanogen-containing compounds and other additives.

Advantageously the inventive compounds or mixtures thereof are applied in the form of preparations such as powders, dusts, granulates, solutions, emulsions or suspensions, with addition of liquid and/or solid carrier materials or thinners and if desired with emulsifiers, dispersants, adhesives and/or wetting agents.

As solid carrier material are suitable such substances as mineral earths, such as tonsil, silica gel, talcum, kaolin, attaclay, calcite, and silica, and plant products, such as flours.

Suitable liquid carriers include water, aliphatic and aromatic hydrocarbons such as benzene, toluene, xylene, cyclohexanone, isophorone, dimethylsulfoxide, and dimethylformamide, as well as mineral oil fractions.

As useful surface active agents should be mentioned as examples calcium lignin sulfonate, polyoxyethylenealkyl phenol ether, naphthalene sulfonic acid and salts thereof, phenol sulfonic acids and salts thereof, formaldehyde condensates, fatty alcohol sulfates as well as substituted benzene sulfonic acids and salts thereof.

The amount of active agent or agents in the various preparations can be varied within a wide range. By example, the agents contain between about 10 and 80 weight-% active agent, between about 90 to 20 weight-% liquid or solid carrier material as well as if desired up to 20 weight-% of surface active ingredients.

Application of the compositions can be effected in conventional manner, for example, with water as carrier in spray amounts of about 100 to 1000 liter/ha. Application of the compositions in the so-called Low-Volume- and Ultra-Low-Volume-Processes is also possible, as is their application in the form of so-called microgranulates.

The novel diurethanes according to the invention may be prepared, for example by (a) reacting a compound of the general formula

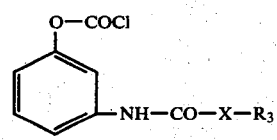

with an amine of the general formula

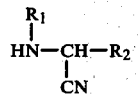

in the presence of an acid acceptor, for example, with addition of excess amine, or an inorganic base like sodium hydroxide or potassium carbonate, or a tertiary organic base, such as triethylamine; or (b) reacting a compound of the general formula

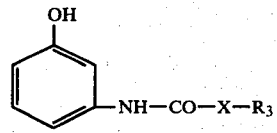

in the presence of a tertiary organic base such as triethylamine or pyridine, or as the alkali salt, with carbamoyl chlorides of the general formula

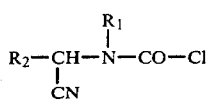

at temperatures between about 0°–100° C., where $R_1$, $R_2$ and $R_3$ have the above meaning.

The invention may be better understood through the following examples.

EXAMPLE 1

N-(1-cyano-2-phenylpropyl)-N-methylcarbaminic acid-3-(methoxycarbonylamino)-phenyl ester Into a solution of 17.4 g (0.1 Mol) 2-methylamino-3-phenyl-butyronitrile in 100 ml ethyl acetate a solution of 22.9 g (0.1 Mol) chloroformic acid-3-methoxycarbonylaminophenyl ester in 50 ml ethyl acetate and simultaneously a solution of 13.8 g (0.1 Mol) potassium carbonate in 50 ml water are added dropwise wtih cooling to about 10° to 15° and with stirring. The organic phase is separated, washed with diluted hydrochloric acid at 0° C. and water, dried with magnesium sulfate and concentrated under reduced pressure. The product is crystallized from ethyl acetate/pentane.

Yield: 28.9 g = 79% of theory.
M.P.: 121° C.

in an analogous manner the following inventive compounds can be prepared.

| Compound | Physical Constants |
|---|---|
| α-Cyanobenzyl-carbaminic acid-[3-(methoxy-carbonylamino)phenyl]-ester | M.P.: 168° C. |
| α-Cyanobenzyl)-carbaminic acid-[3-(ethoxycarbonylamino)-phenyl]-ester | M.P.: 180° C. |
| α-Cyanobenzyl-carbaminic acid-[3-(methylthiocarbonylamino)-phenyl]-ester | M.P.: 188° C. |
| α-Cyanobenzyl-carbaminic acid-[3-(ethylthiocarbonylamino)-phenyl]-ester | M.P.: 199° C. |
| α-Cyanobenzyl-carbaminic acid-[3-(1-methylethoxycarbonylamino)-phenyl]-ester | M.P.: 185° C. |
| α-Cyanobenzyl-carbaminic acid-[3-(2-methylpropoxycarbonylamino)-phenyl]-ester | M.P.: 178° C. |
| α-Cyanobenzyl-carbaminic acid-[3-(1-methylpropoxycarbonylamino)-phenyl]-ester | M.P.: 162° C. |
| α-Cyanobenzyl-N-butyl-carbaminic acid-[3-(methylthio-carbonylamino)-phenyl]-ester | M.P.: 96° C. |
| α-Cyanobenzyl-N-(2-methylpropyl)-carbaminic acid-[3-(methoxycarbonylamino)-phenyl]-ester | M.P.: 95° C. |
| α-Cyanobenzyl-N-(2-methylpropyl)-carbaminic acid-[3-(methylthio-carbonylamino)-phenyl]-ester | M.P.: 110° C. |
| α-Cyanobenzyl-N-butyl-carbaminic acid-[3-(2-methylpropoxycarbonylamino)-phenyl]-ester | M.P.: 69° C. |
| α-Cyanobenzyl-N-butyl-carbaminic acid-[-(1-methylpropoxycarbonylamino)-phenyl]-ester | $n_D20$ 1,5210 |
| α-Cyanobenzyl-N-(2-methylpropyl)-carbaminic acid-[3-(2-methylpropoxycarbonylamino)-phenyl]-ester | M.P.: 70° C. |
| α-Cyanobenzyl-N-butyl-carbaminic acid-[3-(allyloxycarbonylamino)-phenyl]-ester | M.P.: 81° C. |
| α-Cyanobenzyl-N-butyl-carbaminic acid-[3-(methoxycarbonylamino)-phenyl]-ester | M.P.: 61° C. |
| α-Cyanobenzyl-N-butyl-carbaminic acid-[3-(ethoxycarbonylamino)-phenyl]-ester | M.P.: 71° C. |
| α-Cyanobenzyl-N-methyl-carbaminic acid-[3-(methoxycarbonylamino)-phenyl]-ester | $n_D20$ 1,5581 |
| α-Cyanobenzyl-N-methyl-carbaminic acid-[3-(allyloxycarbonylamino)-phenyl]-ester | M.P.: 123° C. |
| α-Cyanobenzyl-N-methyl-carbaminic acid-[3-(2-methylpropoxycarbonylamino)-phenyl]-ester | M.P.: 93° C. |
| α-Cyanobenzyl-N-ethyl-carbaminic acid-[3-(allyloxycarbonylamino)-phenyl]-ester | M.P.: 98° C. |
| α-Cyanobenzyl-N-methylcarbaminic acid-[3-(ethoxycarbonylamino)-phenyl]-ester | M.P.: 113° C. |
| α-Cyanobenzyl-N-methyl-carbaminic acid-[3-(ethylthiocarbonylamino)-phenyl]-ester | M.P.: 94° C. |
| α-Cyanobenzyl-N-ethyl-carbaminic acid-[3-(ethoxycarbonylamino)-phenyl]-ester | M.P.: 96° C. |
| α-Cyanobenzyl-N-ethyl-carbaminic acid-[3-(ethylthiocarbonylamino)-phenyl]-ester | M.P.: 100° C. |
| α-Cyanobenzyl-N-ethyl-carbaminic acid-[3-(2-methylpropoxycarbonylamino)-phenyl]-ester | M.P.: 92° C. |
| α-Cyanobenzyl-N-ethyl-carbaminic acid-[3-(methylthiocarbonylamino)-phenyl]-ester | M.P.: 94° C. |
| α-Cyanobenzyl-N-allylcarbaminic acid-[3-(methoxycarbonylamino)-phenyl]-ester | M.P.: 81° C. |
| α-Cyanobenzyl-N-allyl-carbaminic acid-[3-(ethoxycarbonylamino)-phenyl]-ester | M.P.: 76° C. |
| α-Cyanobenzyl-N-allyl-carbaminic acid-[3-(ethylthiocarbonylamino)-phenyl]-ester | M.P.: 96°–98° C. |
| α-Cyanobenzyl-N-allyl-carbaminic acid-[3-allyloxycarbonylamino)-phenyl]-ester | M.P.: 86° C. |
| N-(α-Cyanobenzyl)-N-allyl-carbaminic acid-[3-(2-propinyloxycarbonylamino)-phenyl]-ester | M.P.: 83° C. |
| N-(α-Cyanobenzyl)-N-ethyl-carbaminic acid-[3-(2-propinyloxycarbonylamino)-phenyl]-ester | M.P.: 94° C. |
| N-(α-Cyano-4-methylbenzyl)-N-ethyl-carbaminic acid-[3-(methoxycarbonylamino)-phenyl]-ester | M.P.: 117° C. |
| N-(α-Cyano-4-methylbenzyl)-N-ethyl-carbaminic acid-[3-(ethoxycarbonylamino)-phenyl]-ester | M.P.: 120° C. |
| N-(α -Cyano-4-methylbenzyl)-N-ethyl-carbaminic acid-[3-(ethylthiocarbonylamino)-phenyl]-ester | M.P.: 160° C. |
| N-(α-Cyano-4-methylbenzyl)-N-ethyl-carbaminic acid-[3-(1-methylethoxycarbonylamino)-phenyl]-ester | M.P.: 125° C. |
| N-(α-Cyano-4-methylbenzyl)-N-ethyl-carbaminic acid-[3-(allyloxycarbonylamino)-phenyl]-ester | M.P.: 103° C. |
| N-(α-Cyano-4-methylbenzyl)-N-ethyl-carbaminic acid-[3-(2-methylpropoxycarbonylamino)-phenyl]-ester | M.P.: 109° C. |
| N-(α-Cyano-4-methylbenzyl)-N-ethyl-carbaminic acid-[3-(2-propinyloxycarbonylamino)-phenyl]-ester | M.P.: 114° C. |
| N-(α-Cyano-3-methylbenzyl)-N-ethyl-carbaminic acid-[3-(methoxycarbonylamino)-phenyl]-ester | M.P.: 113° C. |
| N-(α-Cyano-3-methylbenzyl)-N-ethyl-carbaminic acid-[3-(ethoxycarbonylamino)-phenyl]-ester | M.P.: 93° C. |
| N-(α-Cyano-3-methylbenzyl)-N-ethyl-carbaminic acid-[3-(2-propinyloxycarbonylamino) phenyl]-ester | M.P.: 84° C. |
| N-(α-Cyanobenzyl)-N-methyl-carbaminic acid-[3-(1-methylethoxycarbonylamino)-phenyl]-ester | M.P.: 96° C. |
| N-(α-Cyano-3-methylbenzyl)-N-ethylcarbaminic acid-[3-(allyloxycarbonylamino)-phenyl]-ester | M.P.: 79° C. |
| N-(α-Cyano-3-methylbenzyl)-N-ethylcarbaminic acid-[3-(ethylthiocarbonylamino)-phenyl]-ester | M.P.: 144° C. |
| N-(α-Cyano-3-methylbenzyl)-N-ethyl-carbaminic acid-[3-(1-methylethoxycarbonylamino)-phenyl]-ester | M.P.: 95° C. |

| Compound | Physical Constants |
|---|---|
| N-(α-Cyano-3-methylbenzyl)-N-ethyl-carbaminic acid-[3-(2-methylpropoxycarbonylamino)-phenyl]-ester | M.P.: 93° C. |
| N-(α-Cyanobenzyl)-N-methyl-carbaminic acid-[3-(2-propinyloxycarbonylamino]-ester | M.P.: 98° C. |
| N-(α-Cyanobenzyl)-N-methyl-carbaminic acid-[3-(1-methylpropoxycarbonylamino)-phenyl]-ester | M.P.: 96° C. |
| N-(α-Cyanobenzyl)-N-ethyl-carbaminic acid-[3-(1-methylethoxycarbonylamino)-phenyl]-ester | M.P.: 88° C. |
| N-(α-Cyano-4-methoxybenzyl)-N-ethyl-carbaminic acid-[3-(ethoxycarbonylamino)-phenyl]-ester | M.P.: 95° C. |
| N-(α-Cyano-4-methoxybenzyl)-N-ethyl-carbaminic acid-[3-ethylthiocarbonylamino)-phenyl]-ester | M.P.: 115° C. |
| N-(α-Cyano-4-methoxybenzyl)-N-ethyl-carbaminic acid-[3-(1-methylethoxycarbonylamino)-phenyl]-ester | M.P.: 97° C. |
| N-(α-Cyano-4-methoxybenzyl)-N-ethyl-carbaminic acid-[3-(2-methylpropoxycarbonylamino)-phenyl]-ester | M.P.: 93° C. |
| N-(α-Cyano-4-methoxybenzyl)-N-ethyl-carbaminic acid-[3-(2-propinyloxycarbonylamino)-phenyl]-ester | M.P.: 94° C. |
| N-(α-Cyano-4-methoxybenzyl)-N-ethyl-carbaminic acid -[3-(methylthiocarbonylamino)-phenyl]-ester | M.P.: 164° C. |
| N-(α-Cyano-4-methoxybenzyl)-N-ethyl-carbaminic acid-[3-(methylthiocarbonylamino)-phenyl]-ester | M.P.: 103° C. |
| N(α-Cyano-4-chlorobenzyl)-N-ethyl-carbaminic acid-[3-(methoxycarbonylamino)-phenyl]-ester | M.P.: 136° C. |
| N-(α-Cyano-4-chlorobenzyl)-N-ethyl-carbaminic acid-[3-(methylthiocarbonylamino)-phenyl]-ester | M.P.: 150° C. |
| N-(α-Cyano-4-chlorobenzyl)-N-ethyl-carbaminic acid-[3-(ethoxycarbonylamino)-phenyl]-ester | M.P.: 155° C. |
| N-(α-Cyano-4-chlorobenzyl)-N-ethyl-carbaminic acid-[3-(allyloxycarbonylamino)-phenyl]-ester | M.P.: 100° C. |
| N-(α-Cyano-4-chlorobenzyl)-N-ethyl-carbaminic acid-[3-(ethylthiocarbonylamino)-phenyl]-ester | M.P.: 154° C. |
| N-(α-Cyano-4-chlorobenzyl)-N-methyl-carbaminic acid-[3-(methoxycarbonylamino)-phenyl]-ester | M.P.: 108° C. |
| N-(α-Cyano-benzyl)-N-ethyl-carbaminic acid-[3-(methoxycarbonylamino)-phenyl]-ester | M.P.: 82° C. |
| N-(α-Cyano-benzyl)-N-ethyl-carbaminic acid-[3-(1-methylpropoxycarbonylamino)-phenyl]-ester | $n_D20$ 1,5326 |
| N-(α-Cyano-benzyl)-N-allyl-carbaminic acid-[3-(1-methylethoxycarbonylamino)-phenyl]-ester | $n_D20$ 1,5413 |
| N-(α-Cyano-benzyl)-N-allyl-carbaminic acid-[3-(2-methylpropoxycarbonylamino)-phenyl]-ester | M.P.: 84° C. |
| N-(α-Cyano-3,4-dichlorobenzyl)-N-ethyl-carbaminic acid-[3-(2-methylpropoxycarbonylamino)-phenyl]-ester | M.P.: 94° C. |
| N-(α-Cyano-3-chloro-benzyl)-N-ethyl-carbaminic acid-[3-(1-methylethoxycarbonylamino)-phenyl]-ester | M.P.: 128° C. |
| N-(α-Cyano-cyclohexyl-methyl)-N-methyl-carbaminic acid-[3-(methoxycarbonylamino)-phenyl]-ester | M.P.: 145° C. |
| N-(α-Cyano-cyclohexylmethyl)-N-methyl-carbaminic acid-[3-(ethylthiocarbonylamino)-phenyl]-ester | M.P.: 114° C. |
| N-(α-Cyano-cyclohexylmethyl)-N-methyl-carbaminic acid-[3-(2-methylpropoxycarbonylamino)-phenyl]-ester | M.P.: 116° C. |
| N-(α-Cyano-3-methoxybenzyl)-N-methyl-carbaminic acid-[3-(methylthiocarbonylamino)-phenyl]-ester | M.P.: 120° C. |
| N-(α-Cyano-3-methoxy-benzyl)-N-methylcarbaminic acid-[3-allyloxycarbonylamino)-phenyl]-ester | M.P.: 120° C. |
| N-(α-Cyano-3-methoxy-benzyl)-N-methylcarbaminic acid-[3-(2-propinyloxycarbonylamino)-phenyl]-ester | M.P.: 109° C. |
| N-(α-Cyano-3-methoxy-benzyl)-N-methylcarbanilic acid-[3-(2-methylpropoxycarbonylamino)-phenyl]-ester | M.P.: 92° C. |
| N-(1-Cyano-2-phenyl-ethyl)-N-methyl-carbaminic acid-[3-(2-propinyloxycarbonylamino)-phenyl]-ester | M.P.: 94° C. |
| N-(α-Cyano-3,4-dichlorobenzyl)-N-ethyl-carbaminic acid-[3-(methoxycarbonylamino)-phenyl]-ester | M.P.: 101–103° C. |
| N-(α-Cyano-3-chlorobenzyl)-N-ethyl-carbaminic acid-[3-(methoxycarbonylamino)-phenyl]-ester | M.P.: 91° C. |
| N-(α-Cyano-3-methoxy-benzyl)-N-methylcarbaminic acid-[3-(methoxycarbonylamino)-phenyl]-ester | M.P.: 107° C. |
| N-(1-Cyano-2-phenyl-ethyl)-N-methylcarbaminic acid-[3-(methoxycarbonylamino)-phenyl]-ester | M.P.: 84° C. |
| N-(α-Cyanobenzyl)-N-ethyl-carbaminic acid-[3-(4-chloro-2-butinyloxycarbonylamino)-phenyl]-ester | $n_D20$ 1,5465 |
| N-(1-Cyano-2-phenyl-ethyl)-N-methyl-carbaminic acid-[3-(allyloxycarbonylamino)-phenyl]-ester | M.P.: 79° C. |
| N-(α-Cyano-2,6-dichlorobenzyl)-N-methylcarbaminic acid-[3-(methoxycarbonylamino)-phenyl]-ester | M.P.: 122° C. |
| N-(α-Cyano-2,6-dichlorobenzyl)-N-methylcarbaminic acid-[3-(methylthiocarbonylamino)-phenyl]-ester | M.P.: 198° C. |
| N-(α-Cyano-2,6-dichlorobenzyl)-N-methylcarbaminic acid-[3-(2-propinyloxycarbonylamino)-phenyl]-ester | M.P.: 118° C. |
| N-(1-Cyano-2-phenyl-ethyl)-N-methyl-carbaminic acid-[3-(methylthiocarbonylamino)-phenyl]-ester | M.P.: 103–105° C. |
| N-(α-Cyano-2,6-dichlorobenzyl)-N-methyl-carbaminic acid-[3-(allyloxycarbonylamino)-phenyl]-ester | M.P.: 87–88° C. |
| N-(α-Cyano-2,4-dichlorobenzyl)-N-methyl-carbaminic acid-[3-(methoxycarbonylamino)-phenyl]-ester | M.P.: 169–170° C. |
| N-(α-Cyano-2,4-dichlorobenzyl)-N-methylcarbaminic acid-[3-(methylthiocarbonylamino)-phenyl]-ester | M.P.: 143–144° C. |
| N-(α-Cyano-2,4-dichlorobenzyl)-N-methylcarbaminic acid-[3-(allyloxycarbonylamino)-phenyl]-ester | M.P.: 126–127° C. |
| N-(α-Cyano-2,4-dichlorobenzyl)-N-methylcarbaminic acid-[3-(2-propinyloxycarbonylamino)-phenyl]-ester | M.P.: 151–152° C. |
| N-(α-Cyano-3-chlorobenzyl)-N-ethylcarbaminic acid-[3-(allyloxycarbonylamino)-phenyl]-ester | M.P.: 107–110° C. |
| N-(α-Cyano-3-chlorobenzyl)-N-ethylcarbaminic acid-[3-(2-propinyloxycarbonylamino)-phenyl]-ester | M.P.: 104–105° C. |
| N-(α-Cyano-3-chlorobenzyl)-N-ethylcarbaminic acid-[3-(methylthiocarbonylamino)-phenyl]-ester | M.P.: 137° C. |
| N-(1-Cyano-2-phenyl-propyl)-N-methylcarbaminic acid-[3-(ethoxycarbonylamino)-phenyl]-ester | M.P.: 120° C. |
| N-(1-Cyano-2-phenyl-propyl)-N-methyl-carbaminic acid-[3-(methylthiocarbonylamino)-phenyl]-ester | M.P.: 108° C. |
| N-(α-Cyano-3-chlorobenzyl)-N-ethylcarbaminic acid-3-(ethoxycarbonylamino)-phenyl-ester | M.P.: 131° C. |
| N-(α-Cyano-3,4-dichlorobenzyl)-N-methyl-carbaminic acid-[3-methoxycarbonylamino)-phenyl]-ester | M.P.: 118–119° C. |
| N-(α-Cyano-3,4-dichlorobenzyl)-N-methylcarbaminic acid-[3-(ethoxycarbonylamino)-phenyl]-ester | M.P.: 104° C. |
| N-(α-Cyano-3,4-dichlorobenzyl)-N-methylcar- | M.P.: |

| Compound | Physical Constants |
|---|---|
| baminic acid-[3-(methylthiocarbonylamino)-phenyl]-ester | 138° C. |
| N-(α-Cyano-3,4-dichlorobenzyl)-N-methylcarbaminic acid-[3-(allyloxycarbonylamino)-phenyl]-ester | M.P.: 116–117° C. |
| N-(α-Cyano-3,4-dichlorobenzyl)-N-methyl-carbaminic acid-[3-(2-propinyloxycarbonylamino)-phenyl]-ester | M.P.: 145° C. |
| N-(1-Cyano-2-phenylpropyl)-N-methylcarbaminic acid-[3-(2-propinyloxycarbonylamino)-phenyl]-ester | M.P.: 134–135° C. |
| N-(1-Cyano-2-phenylpropyl)-N-methylcarbaminic acid-[3-(allyloxycarbonylamino)-phenyl]-ester | $n_D 20$ 1,5420 |
| N-(1-Cyano-2-phenylpropyl)-N-methyl-carbaminic acid-[3-(ethylthiocarbonylamino)-phenyl]-ester | M.P.: 114–116° C. |
| N-(α-Cyano-3-chlorobenzyl)-N-methylcarbaminic acid-[3-(methoxycarbonylamino)-phenyl]-ester | M.P.: 122–123° C. |
| N-(1-Cyano-2-phenylpropyl)-N-methylcarbaminic acid-[3-(1-methylethoxycarbonylamino)-phenyl]-ester | M.P.: 115–116° C. |
| N-(α-Cyano-3-chlorobenzyl)-N-methylcarbaminic acid-[3-(ethoxycarbonylamino)-phenyl]-ester | M.P.: 129–130° C. |
| N-(α-Cyano-3-chlorobenzyl)-N-methylcarbaminic acid-[3-(methylthiocarbonylamino)-phenyl]-ester | M.P.: 130–133° C. |
| N-(α-Cyano-3-chlorobenzyl)-N-methylcarbaminic acid-[ 3-(ethylthiocarbonylamino)-phenyl]-ester | M.P.: 122° C. |
| N-(α-Cyano-3-chlorobenzyl)-N-methylcarbaminic acid-[3-(1-methylethoxycarbonylamino)-phenyl]-ester | M.P.: 127° C. |
| N-(α-Cyano-3-chlorobenzyl)-N-methylcarbaminic acid-[3-(allyloxycarbonylamino)-phenyl]-ester | M.P.: 125° C. |
| N-(α-Cyano-3-chlorobenzyl)-N-methylcarbaminic acid-[3-(2-propinyloxycarbonylamino)-phenyl]-ester | M.P.: 100–103° C. |
| N-(1-Cyano-2-phenylethyl)-N-methylcarbaminic acid-[3-(ethylthiocarbonylamino)-phenyl]-ester | M.P.: 112° C. |
| N-(1-Cyano-2-phenylpropyl)-N-methylcarbaminic acid-[3-(2-methylpropoxycarbonylamino)-phenyl]-ester | $n_D 20$: 1,5271 |

These compounds are soluble in acetone, cyclohexanone, ethyl acetate, isophorone, ether and tetrahydrofuran and practically insoluble in water and light gasoline.

The compounds used as starting material for the inventive compounds can be prepared according to known methods; for example, from the corresponding aldehyde, potassium cyanide and the hydrochloride of the corresponding amine.

The following examples serve to illustrate the possibilities for use of the inventive diurethanes and to show the exceptional selective herbicidal properties of the compounds.

EXAMPLE 2

In a greenhouse the compounds listed in the table were applied, at an application rate of 5 kg active agent/ha, dissolved in 500 liters water/ha, on mustard and tomato plants in post-emergence tests.

Three weeks after the treatment the results are determined, whereby

0=no effect and

4=total damage to the plants.

As can be seen from the table, as a rule a destruction of the test plants was achieved.

| Compound of the Invention | Brassica- | Solanum |
|---|---|---|
| α-Cyanobenzyl-carbaminic acid-[3-(methoxycarbonylamino)-phenyl]-ester | 4 | 4 |
| α-Cyanobenzyl-carbaminic acid-[3-(ethoxycarbonylamino)-phenyl]-ester | 4 | 4 |
| α-Cyanobenzyl-carbaminic acid-[3-(methylthiocarbonylamino)-phenyl]-ester | 4 | 4 |
| α-Cyanobenzyl-carbaminic acid-[3-(ethylthiocarbonylamino)-phenyl]-ester | 4 | 4 |
| α-Cyanobenzyl-carbaminic acid-[3-(1-methylethoxycarbonylamino)-phenyl]-ester | 4 | 4 |
| α-Cyanobenzyl-carbaminic acid-[3-(2-methylpropoxycarbonylamino)-phenyl]-ester | 4 | 4 |
| α-Cyanobenzyl-carbaminic acid-[3-(1-methylpropoxycarbonylamino)-phenyl]-ester | 4 | 4 |
| α-Cyanobenzyl-N-butyl-carbaminic acid-[3-(methylthio-carbonylamino)-phenyl]-ester | 4 | 4 |
| α-Cyanobenzyl-N-(2-methylpropyl)-carbaminic acid-[3-(methoxycarbonylamino)-phenyl]-ester | 4 | 4 |
| α-Cyanobenzyl-N-(2-methylpropyl)-carbaminic acid-[3-(methylthio-carbonylamino)-phenyl]-ester | 4 | 4 |
| α-Cyanobenzyl-N-butyl-carbaminic acid-[3-(2-methylpropoxycarbonylamino)-phenyl]-ester | 4 | 4 |
| α-Cyanobenzyl-N-butyl-carbaminic acid-[(1-methylpropoxycarbonylamino)-phenyl]-ester | 4 | 4 |
| α-Cyanobenzyl-N-(2-methylpropyl)-carbaminic acid-[3-(2-methylpropoxycarbonylamino)-phenyl]-ester | 4 | 4 |
| α-Cyanobenzyl-N-butyl-carbaminic acid-[3-(allyloxycarbonylamino)-phenyl]-ester | 4 | 4 |
| α-Cyanobenzyl-N-butyl-carbaminic acid-[3-(methoxycarbonylamino)-phenyl]-ester | 4 | 4 |
| α-Cyanobenzyl-N-butyl-carbaminic acid-[3-(ethoxycarbonylamino)-phenyl]-ester | 4 | 4 |
| α-Cyanobenzyl-N-methyl-carbaminic acid-[3-(methoxycarbonylamino)-phenyl]-ester | 4 | 4 |
| α-Cyanobenzyl-N-methyl-carbaminic acid-[3-(allyloxycarbonylamino)-phenyl]-ester | 4 | 4 |
| α-Cyanobenzyl-N-methyl-carbaminic acid-[3-(2-methylpropoxycarbonylamino)-phenyl]-ester | 4 | 4 |
| α-Cyanobenzyl-N-ethyl-carbaminic acid-[3-(allyloxycarbonylamino)-phenyl] -ester | 4 | 4 |
| α-Cyanobenzyl-N-methylcarbaminic acid-[3-(ethoxycarbonylamino)-phenyl]-ester | 4 | 4 |
| α-Cyanobenzyl-N-methylcarbaminic acid-[3-(ethylthiocarbonylamino)-phenyl]-ester | 4 | 4 |
| α-Cyanobenzyl-N-ethyl-carbaminic acid-[3-(ethoxycarbonylamino)-phenyl]-ester | 4 | 4 |
| α-Cyanobenzyl-N-ethyl-carbaminic acid-[3-(ethylthiocarbonylamino)-phenyl]-ester | 4 | 4 |
| α-Cyanobenzyl-N-ethyl-carbaminic acid-[3-(2-methylpropoxycarbonylamino)-phenyl]-ester | 4 | 4 |
| α-Cyanobenzyl-N-ethyl-carbaminic acid-[3-(methylthiocarbonylamino)-phenyl]-ester | 4 | 4 |
| α-Cyanobenzyl-N-allyl-carbaminic acid-[3-(methoxycarbonylamino)-phenyl]-ester | 4 | 4 |
| α-Cyanobenzyl-N-allyl-carbaminic acid-[3-(ethoxycarbonylamino)-phenyl]-ester | 4 | 4 |
| α-Cyanobenzyl-N-allyl-carbaminic acid-[3-(ethylthiocarbonylamino)-phenyl]-ester | 4 | 4 |
| α-Cyanobenzyl-N-allyl-carbaminic acid-[3-allyloxycarbonylamino)-phenyl]-ester | 4 | 4 |
| N-(α-Cyanobenzyl)-N-allyl-carbaminic acid-[3-(2-propinyloxycarbonylamino)-phenyl]-ester | 4 | 4 |
| N-(α-Cyanobenzyl)-N-ethyl-carbaminic-[3-(2-propinyloxycarbonylamino)-phenyl]-ester | 4 | 4 |
| N-(α-Cyano-4-methylbenzyl)-N-ethyl-carbaminic acid-[3-(methoxycarbonylamino)-phenyl]-ester | 4 | 4 |
| N-(α-Cyano-4-methylbenzyl)-N-ethyl-carbaminic acid-[3-(ethoxycarbonylamino)-phenyl]-ester | 4 | 4 |
| N-(α-Cyano-4-methylbenzyl)-N-ethyl-carbaminic acid-[3-(ethylthiocarbonylamino)-phenyl]-ester | 4 | 4 |
| N-(α-Cyano-4-methylbenzyl)-N-ethyl-carbaminic acid-[3-(1-methylethoxycarbonylamino)-phenyl]-ester | 4 | 4 |
| N-(α-Cyano-4-methylbenzyl)-N-ethyl-carbaminic acid-[3-(allyloxycarbonylamino)-phenyl]-ester | 4 | 4 |
| N-(α-Cyano-4-methylbenzyl)-N-ethyl-carbaminic acid-[3-(2-methylpropoxycarbonylamino)-phenyl]-ester | 4 | 4 |
| N-(α-Cyano-4-methylbenzyl)-N-ethyl-carbaminic | | |

-continued

| Compound of the Invention | Brassica | Solanum |
|---|---|---|
| acid-[3-(2-propinyloxycarbonylamino)-phenyl]-ester | 4 | 4 |
| N-(α-Cyano-3-methylbenzyl)-N-ethyl-carbaminic acid-[3-(methoxycarbonylamino)-phenyl]-ester | 4 | 4 |
| N-(α-Cyano-3-methylbenzyl)-N-ethyl-carbaminic acid-[3-(ethoxycarbonylamino)-phenyl]-ester | 4 | 4 |
| N-(α-Cyano-3-methylbenzyl)-N-ethyl-carbaminic acid-[3-(2-propinyloxycarbonylamino)-phenyl]-ester | 4 | 4 |
| N-(α-Cyanobenzyl)-N-methyl-carbaminic acid-[3-(1-methylethoxycarbonylamino)-phenyl]-ester | 4 | 4 |
| N-(α-Cyano-3-methylbenzyl)-N-ethylcarbaminic acid-[3-(allyloxycarbonylamino)-phenyl]-ester | 4 | 4 |
| N-(α-Cyano-3-methylbenzyl)-N-ethylcarbaminic acid-[3-ethylthiocarbonylamino)-phenyl]-ester | 4 | 4 |
| N-(α-Cyano-3-methylbenzyl)-N-ethyl-carbaminic acid-[3-(1-methylethoxycarbonylamino)-phenyl]-ester | 4 | 4 |
| N-(α-Cyano-3-methylbenzyl)-N-ethyl-carbaminic acid-[3-(2-methylpropoxycarbonylamino)-phenyl]-ester | 4 | 4 |
| N-(α-Cyanobenzyl)-N-methyl-carbaminic acid-[3-(2-propinyloxycarbonylamino)-phenyl]-ester | 4 | 4 |
| N-(α-Cyanobenzyl)-N-methyl-carbaminic acid-[3-(1-methylpropoxycarbonylamino)-phenyl]-ester | 4 | 4 |
| N-(α-Cyanobenzyl)-N-ethyl-carbaminic acid-[3-(1-methylethoxycarbonylamino)-phenyl]-ester | 4 | 4 |
| N-(α-Cyano-4-methoxybenzyl)-N-ethyl-carbaminic acid-[3-(ethoxycarbonylamino)-phenyl]-ester | 4 | 4 |
| N-(α-Cyano-4-methoxybenzyl)-N-ethyl-carbaminic acid-[3-(ethylthiocarbonylamino)-phenyl]-ester | 4 | 4 |
| N-(α-Cyano-4-methoxybenzyl)-N-ethyl-carbaminic acid-[3-(1-methylethoxycarbonylamino)-phenyl]-ester | 4 | 4 |
| N-(α-Cyano-4-methoxybenzyl)-N-ethyl-carbaminic acid-[3-(2-methylpropoxycarbonylamino)-phenyl]-ester | 4 | 4 |
| N-(α-Cyano-4-methoxybenzyl)-N-ethyl-carbaminic acid-[3-(2-propinyloxycarbonylamino)-phenyl]-ester | 4 | 4 |
| N-(α-Cyano-4-methoxybenzyl)-N-ethyl-carbaminic acid-[3-(methylthiocarbonylamino)-phenyl]-ester | 4 | 4 |
| N-(α-Cyano-4-methoxybenzyl)-N-ethyl-carbaminic acid-[3-(methylthiocarbonylamino)-phenyl]-ester | 4 | 4 |
| N-(α-Cyano-4-chlorobenzyl)-N-ethyl-carbaminic acid-[3-(methoxycarbonylamino)-phenyl]-ester | 4 | 4 |
| N-(α-Cyano-4-chlorobenzyl)-N-ethyl-carbaminic acid-[3-(methylthiocarbonylamino)-phenyl]-ester | 4 | 4 |
| N-(α-Cyano-4-chlorobenzyl)-N-ethyl-carbaminic acid-[3-(ethoxycarbonylamino)-phenyl]-ester | 4 | 4 |
| N-(α-Cyano-4-chlorobenzyl)-N-ethyl-carbaminic acid-[3-(allyloxycarbonylamino)-phenyl]-ester | 4 | 4 |
| N-(α-Cyano-4-chlorobenzyl)-N-ethyl-carbaminic acid-[3-(ethylthiocarbonylamino)-phenyl]-ester | 4 | 4 |
| N-(α-Cyano-4-chlorobenzyl)-N-ethyl-carbaminic acid-[3-(methoxycarbonylamino)-phenyl]-ester | 4 | 4 |
| N-(α-Cyano-benzyl)-N-ethyl-carbaminic acid-[3-(methoxycarbonylamino)-phenyl]-ester | 4 | 4 |
| N-(α-Cyano-benzyl)-N-ethyl-carbaminic acid-[3-(1-methylpropoxycarbonylamino)-phenyl]-ester | 4 | 4 |
| N-(α-Cyano-benzyl)-N-allyl-carbaminic acid-[3-(1-methylethoxycarbonylamino)-phenyl]-ester | 4 | 4 |
| N-(α-Cyano-benzyl)-N-allyl-carbaminic acid-[3-(2-methylpropoxycarbonylamino)-phenyl]-ester | 4 | 4 |
| N-(α-Cyano-3,4-dichlorobenzyl)-N-ethyl-carbaminic acid-[3-(2-methylpropoxycarbonylamino)-phenyl]-ester | 4 | 4 |
| N-(α-Cyano-3-chloro-benzyl)-N-ethyl-carbaminic acid-[3-(1-methylethoxycarbonylamino)-phenyl]-ester | 4 | 4 |
| N-(α-Cyano-cyclohexyl-methyl)-N-methyl-carbaminic acid-[3-(methoxycarbonylamino)-phenyl]-ester | 4 | 4 |
| N-(α-Cyano-cyclohexylmethyl)-N-methyl-carbaminic acid-[3-(ethylthiocarbonylamino)-phenyl]-ester | 4 | 4 |
| N-(α-Cyano-cyclohexylmethyl)-N-methylcarbaminic acid-[3-(2-methylpropoxycarbonylamino)-phenyl]-ester | 4 | 4 |
| N-(α-Cyano-3-methoxybenzyl)-N-methyl-carbaminic acid-[3-(methylthiocarbonylamino)-phenyl]-ester | 4 | 4 |
| N-(α-Cyano-3-methoxy-benzyl-N-methylcarbaminic acid-[3-(allyloxycarbonylamino)-phenyl]-ester | 4 | 4 |
| N-(α-Cyano-3-methoxy-benzyl)-N-methylcarbaminic acid-[3-(2-propinyloxycarbonylamino)-phenyl]-ester | 4 | 4 |
| N-(α-Cyano-3-methoxy-benzyl)-N-methylcarbanilic acid-[3-(2-methylpropoxycarbonylamino)-phenyl]-ester | | |
| ester | 4 | 4 |
| N-(1-Cyano-2-phenyl-ethyl)-N-methyl-carbaminic acid-[3-(2-propinyloxycarbonylamino)-phenyl]-ester | 4 | 4 |
| N-(α-Cyano-3,4-dichlorobenzyl)-N-ethyl-carbaminic acid-[3-(methoxycarbonylamino)-phenyl]-ester | 4 | 4 |
| N-(α-Cyano-3-chlorobenzyl)-N-ethyl-carbaminic acid-[3-(methoxycarbonylamino)-phenyl]-ester | 4 | 4 |
| N-(α-Cyano-3-methoxy-benzyl)-N-methylcarbaminic acid-[3-(methoxycarbonylamino)-phenyl]-ester | 4 | 4 |
| N-(1-Cyano-2-phenyl-ethyl)-N-methyl-carbaminic acid-[3-(methoxycarbonylamino)-phenyl]-ester | 4 | 4 |
| N-(α-Cyanobenzyl)-N-ethyl-carbaminic acid-[3-(4-chloro-2-butinyloxycarbonylamino)-phenyl]-ester | 4 | 4 |
| N-(1-Cyano-2-phenyl-ethyl)-N-methyl-carbaminic acid-[3-(allyloxycarbonylamino)-phenyl]-ester | 4 | 4 |
| N-(α-Cyano-2,6-dichlorobenzyl)-N-methylcarbaminic acid-[3-(methoxycarbonylamino)-phenyl]-ester | 4 | 4 |
| N-(α-Cyano-2,6-dichlorobenzyl)-N-methylcarbaminic acid-[3-(methylthiocarbonylamino)-phenyl]-ester | 4 | 4 |
| N-(α-Cyano-2,6-dichlorobenzyl)-N-methylcarbaminic acid-[3-(2-propinyloxycarbonylamino)-phenyl]-ester | 4 | 4 |
| N-(1-Cyano-2-phenyl-ethyl)-N-methyl-carbaminic acid-[3-(methylthiocarbonylamino)-phenyl]-ester | 4 | 4 |
| N-(α-Cyano-2,6-dichlorobenzyl)-N-methylcarbaminic acid-[3-(allyloxycarbonylamino)-phenyl]-ester | 4 | 4 |
| N-(α-Cyano-2,4-dichlorobenzyl)-N-methylcarbaminic acid-[3-(methoxycarbonylamino)-phenyl]-ester | 4 | 4 |
| N-(α-Cyano-2,4-dichlorobenzyl)-N-methylcarbaminic acid-[3-(methylthiocarbonylamino)-phenyl]-ester | 4 | 4 |
| N-(α-Cyano-2,4-dichlorobenzyl)-N-methyl-carbaminic acid-[3-(allyloxycarbonylamino)-phenyl]-ester | 4 | 4 |
| N-(α-Cyano-2,4-dichlorobenzyl)-N-methyl-carbaminic acid-[3-(2-propinyloxycarbonylamino)-phenyl]-ester | 4 | 4 |
| N-(α-Cyano-3-chlorobenzyl)-N-ethylcarbaminic acid-[3-(allyloxycarbonylamino)-phenyl]-ester | 4 | 4 |
| N-(α-Cyano-3-chlorobenzyl)-N-ethylcarbaminic acid-[3-(2-propinyloxycarbonylamino)-phenyl]-ester | 4 | 4 |
| N-(α-Cyano-3-chlorobenzyl)-N-ethylcarbaminic acid-[3-(methylthiocarbonylamino)-phenyl]-ester | 4 | 4 |
| N-(1-Cyano-2-phenyl-propyl)-N-methylcarbaminic acid-[3-(ethoxycarbonylamino)-phenyl]-ester | 4 | 4 |
| N-(1-Cyano-2-phenyl-propyl)-N-methyl-carbaminic acid-[3-(methylthiocarbonylamino)-phenyl]-ester | 4 | 4 |
| N-(α-Cyano-3-chlorobenzyl)-N-ethylcarbaminic acid-3-(ethoxycarbonylamino)-phenyl-ester | 4 | 4 |
| N-(α-Cyano-3,4-dichlorobenzyl)-N-methylcarbaminic acid-3-(methoxycarbonylamino)-phenylester | 4 | 4 |
| N-(α-Cyano-3,4-dichlorobenzyl)-N-methylcarbaminic acid-3-(ethoxycarbonylamino)-phenylester | 4 | 4 |
| N-(α-Cyano-3,4-dichlorobenzyl)-N-methylcarbaminic acid-3-(methylthiocarbonylamino)-phenylester | 4 | 4 |
| N-(α-Cyano-3,4-dichlorobenzyl)-N-methylcarbaminic acid-3-(allyloxycarbonylamino)-phenylester | 4 | 4 |
| N-(α-Cyano-3,4-dichlorobenzyl)-N-methylcarbaminic acid-3-(2-propinyloxycarbonylamino)-phenylester | 4 | 4 |
| N-(1-Cyano-2-phenylpropyl)-N-methylcarbaminic acid-3-(2-propinyloxycarbonylamino)-phenylester | 4 | 4 |
| N-(1-Cyano-2-phenylpropyl)-N-methylcarbaminic acid-3-(allyloxycarbonylamino)-phenylester | 4 | 4 |
| N-(1-Cyano-2-phenylpropyl)-N-methylcarbaminic acid-3-(ethylthiocarbonylamino)-phenylester | 4 | 4 |
| N-(α-Cyano-3-chlorobenzyl)-N-methylcarbaminic acid-3-(methoxycarbonylamino)-phenylester | 4 | 4 |
| Untreated | 0 | 0 |

Supplement to Example 2

| Compound of the Invention | Brassica | Solanum |
|---|---|---|
| N-(1-Cyano-2-phenylpropyl)-N-methylcarbaminic acid-[3-(1-methylethoxycarbonylamino)-phenyl]-ester | 4 | 4 |
| N-(α-Cyano-3-chlorobenzyl)-N-methylcarbaminic acid-[3-(ethoxycarbonylamino)-phenyl]-ester | 4 | 4 |
| N-(α-Cyano-3-chlorobenzyl)-N-methylcarbaminic | | |

-continued
Supplement to Example 2

| Compound of the Invention | Brassica | Solanum |
|---|---|---|
| acid-[3-(methylthiocarbonylamino)-phenyl]-ester N-(α-Cyano-3-chlorobenzyl)-N-methylcarbaminic | 4 | 4 |
| acid-[3-(ethylthiocarbonylamino)-phenyl]-ester N-(α-Cyano-3-chlorobenzyl)-N-methylcarbaminic | 4 | 4 |
| acid-[3-(1-methylethoxycarbonylamino)-phenyl]-ester N-(α-Cyano-3-chlorobenzyl)-N-methylcarbaminic | 4 | 4 |

EXAMPLE 3

In a greenhouse the plants were treated post-emergently with the listed agents in an application amount of 1 kg active agent/ha. The agent was to this end sprayed uniformly over the plants. The compounds of the invention show after 3 weeks a high selectivity with a simultaneous effectiveness against the weeds. The comparison agent does not show this selectivity. In the table, 10=no damage and 0=total destruction.

| Compound of the Invention | Sugar beets | Cotton | Peanut | Bush beans | Potatoes | Alfalfa | Rice | Amaranthus | Stellaria | Matricaria | Lamium | Centaurea | Ipomea | Solanum | Brassica |
|---|---|---|---|---|---|---|---|---|---|---|---|---|---|---|---|
| α-Cyanobenzyl-N-methyl-carbaminic acid-[3-(methoxycarbonylamino)-phenyl]-ester | — | 10 | 10 | 10 | 10 | 10 | 10 | 0 | 0 | 3 | 0 | 0 | 0 | 0 | 0 |
| α-Cyanobenzyl-N-methyl-carbaminic acid-[3-(ethoxycarbonylamino)-phenyl]-ester | — | 10 | 10 | 10 | 10 | 10 | 10 | 0 | 0 | 0 | 0 | 0 | 0 | 0 | 0 |
| α-Cyanobenzyl-N-methyl-carbaminic acid-[3-(ethoxycarbonylamino)-phenyl]-ester | — | 10 | 10 | 10 | 10 | 10 | 10 | 0 | 0 | 0 | 0 | 0 | 0 | 0 | 0 |
| α-Cyanobenzyl-N-ethyl-carbaminic acid-[3-(ethoxycarbonylamino)-phenyl]-ester | — | 10 | 10 | 10 | 10 | 10 | 10 | 0 | 0 | 0 | 0 | 0 | 0 | 0 | 0 |
| α-Cyanobenzyl-N-ethyl-carbaminic acid-[3-(ethylthiocarbonylamino)-phenyl]-ester | — | 10 | 10 | 10 | 10 | 10 | 10 | 0 | 0 | 0 | 0 | 0 | 0 | 0 | 0 |
| A-Cyanobenzyl-N-ethyl-carbaminic acid-[3-(methylthiocarbonylamino)-phenyl]-ester | — | 10 | 10 | 10 | 10 | 10 | 10 | 0 | 0 | 0 | 0 | 0 | 0 | 0 | 0 |
| N-(α-Cyano-4-chlorobenzyl)-N-ethyl-carbaminic acid-[3-(methoxycarbonylamino)-phenyl]-ester | — | 10 | 10 | 10 | 10 | 10 | 10 | 0 | 0 | 0 | 0 | 0 | 0 | 0 | 0 |
| N-(α-Cyano-4-chlorobenzyl)-N-ethyl-carbaminic acid-[3-(ethoxycarbonylamino)-phenyl]-ester | — | 10 | 10 | 10 | 10 | 10 | 10 | 0 | 0 | 0 | 0 | 0 | 0 | 0 | 0 |
| N-(α-Cyano-benzyl)-N-ethyl-carbaminic acid-[3-(methoxycarbonylamino)-phenyl]-ester | — | 10 | 10 | 10 | 10 | 10 | 10 | 0 | 0 | 0 | 0 | 0 | 0 | 0 | 0 |
| N-(α-Cyano-cyclohexyl-methyl)-N-methyl-carbaminic acid-[3-methoxycarbonylamino)-phenyl]-ester | 10 | 10 | 10 | 10 | 10 | 10 | 10 | 0 | 0 | 0 | 0 | 0 | 0 | 0 | 0 |
| N-(α-Cyano-cyclohexylmethyl)-N-methyl-carbaminic acid-[3-(ethylthiocarbonylamino)-phenyl]-ester | 10 | 10 | 10 | 10 | 10 | 10 | 10 | 0 | 0 | 0 | 0 | 0 | 0 | 0 | 0 |
| N-(α-Cyano-cyclohexylmethyl)-N-methylcarbaminic acid-[3-(2-methyl-propoxycarbonylamino)-phenyl]-ester | 10 | 10 | 10 | 10 | 10 | 10 | 10 | 0 | 0 | 0 | 0 | 0 | 0 | 0 | 0 |
| Comparison Agent (from DE-PS 1 567 151) 3-Methoxycarbonylamino-phenyl-N-(3-methyl-phenyl)-carbamate | 10 | 5 | 9 | 4 | 8 | 4 | 9 | 8 | 0 | 3 | 0 | 0 | 0 | 0 | 0 |

| | | |
|---|---|---|
| acid-[3-(allyloxycarbonylamino)-phenyl]-ester N-(α-Cyano-3-chlorobenzyl)-N-methylcarbaminic | 4 | 4 |
| acid-[3-(2-propinyloxycarbonylamino)-phenyl]-ester N-(1-Cyano-2-phenylethyl)-N-methylcarbaminic | 4 | 4 |
| acid-[3-(ethylthiocarbonylamino)-phenyl]-ester | 4 | 4 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A compound of the formula

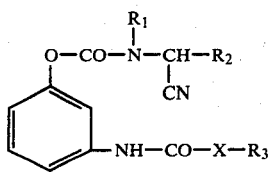

in which
R$_1$ is hydrogen, C$_1$–C$_4$ alkyl or C$_2$–C$_4$ alkenyl;
R$_2$ is phenyl, methylphenyl, methoxyphenyl, chlorophenyl, dichlorophenyl, cyclohexyl, benzyl or phenylethyl;
R$_3$ is C$_1$–C$_4$ alkyl, C$_2$–C$_4$ alkenyl, C$_2$–C$_4$ alkinyl, chloro-C$_1$–C$_4$ alkyl, chloro-C$_2$–C$_4$ alkenyl or chloro-C$_2$–C$_4$ alkinyl; and
X is oxygen or sulfur.

2. A compound as defined in claim 1, which is α-Cyanobenzyl-carbaminic acid-[3-(methoxycarbonylamino)-phenyl]-ester.

3. A compound as defined in claim 1, which is α-Cyanobenzyl-carbaminic acid-[3-(ethoxycarbonylamino)-phenyl]-ester.

4. A compound as defined in claim 1, which is α-Cyanobenzyl-carbaminic acid-[3-(methylthiocarbonylamino)-phenyl]-ester.

5. A compound as defined in claim 1, which is α-Cyanobenzyl-carbaminic acid-[3-(ethylthiocarbonylamino)-phenyl]-ester.

6. A compound as defined in claim 1, which is α-Cyanobenzyl-carbaminic acid-[3-(1-methylethoxycarbonylamino)-phenyl]-ester.

7. A compound as defined in claim 1, which is α-Cyanobenzyl-carbaminic acid-[3-(2-methylpropoxycarbonylamino)-phenyl]-ester.

8. A compound as defined in claim 1, which is α-Cyanobenzyl-carbaminic acid-[3-(1-methylpropoxycarbonylamino)-phenyl]-ester.

9. A compound as defined in claim 1, which is α-Cyanobenzyl-N-butyl-carbaminic acid-[3-(methylthiocarbonylamino)-phenyl]-ester.

10. A compound as defined in claim 1, which is α-Cyanobenzyl-N-(2-methylpropyl)-carbaminic acid-[3-(methoxycarbonylamino)-phenyl]-ester.

11. A compound as defined in claim 1, which is α-Cyanobenzyl-N-(2-methylpropyl)-carbaminic acid-[3-(methylthio-carbonylamino)-phenyl]-ester.

12. A compound as defined in claim 1, which is α-Cyanobenzyl-N-butyl-carbaminic acid-[3-(2-methylpropoxycarbonylamino)-phenyl]-ester.

13. A compound as defined in claim 1, which is α-Cyanobenzyl-N-butyl-carbaminic acid-[-(1-methylpropoxycarbonylamino)-phenyl]-ester.

14. A compound as defined in claim 1, which is α-Cyanobenzyl-N-(2-methylpropyl)-carbaminic acid-[3-(2-methylpropoxycarbonylamino)-phenyl]-ester.

15. A compound as defined in claim 1, which is α-Cyanobenzyl-N-butyl-carbaminic acid-[3-(allyloxycarbonylamino)-phenyl]-ester.

16. A compound as defined in claim 1, which is α-Cyanobenzyl-N-butyl-carbaminic acid-[3-methoxycarbonylamino)-phenyl]-ester.

17. A compound as defined in claim 1, which is α-Cyanobenzyl-N-butyl-carbaminic acid-[3-(ethoxycarbonylamino)-phenyl]-ester.

18. A compound as defined in claim 1, which is α-Cyanobenzyl-N-methyl-carbaminic acid-[3-methoxycarbonylamino)-phenyl]-ester.

19. A compound as defined in claim 1, which is α-Cyanobenzyl-N-methyl-carbaminic acid-[3-(allyloxycarbonylamino)-phenyl]-ester.

20. A compound as defined in claim 1, which is α-Cyanobenzyl-N-methyl-carbaminic acid-[3-(2-methylpropoxycarbonylamino)-phenyl]-ester.

21. A compound as defined in claim 1, which is α-Cyanobenzyl-N-ethyl-carbaminic acid-[3-(allyloxycarbonylamino)-phenyl]-ester.

22. A compound as defined in claim 1, which is α-Cyanobenzyl-N-methylcarbaminic acid-[3-(ethoxycarbonylamino)-phenyl]-ester.

23. A compound as defined in claim 1, which is α-Cyanobenzyl-N-methyl-carbaminic acid-[3-(ethylthiocarbonylamino)-phenyl]-ester.

24. A compound as defined in claim 1, which is α-Cyanobenzyl-N-ethyl-carbaminic acid-[3-(ethoxycarbonylamino)-phenyl]-ester.

25. A compound as defined in claim 1, which is α-Cyanobenzyl-N-ethyl-carbaminic acid-[3-(ethylthiocarbonylamino)-phenyl]-ester.

26. A compound as defined in claim 1, which is α-Cyanobenzyl-N-ethyl-carbaminic acid-[3-(2-methylpropoxycarbonylamino)-phenyl]-ester.

27. A compound as defined in claim 1, which is α-Cyanobenzyl-N-ethyl-carbaminic acid-[3-(methylthiocarbonylamino)-phenyl]-ester.

28. A compound as defined in claim 1, which is α-Cyanobenzyl-N-allyl-carbaminic acid-[3-(methoxycarbonylamino)-phenyl]-ester.

29. A compound as defined in claim 1, which is α-Cyanobenzyl-N-allyl-carbaminic acid-[3-(ethoxycarbonylamino)-phenyl]-ester.

30. A compound as defined in claim 1, which is α-Cyanobenzyl-N-allyl-carbaminic acid-[3-(ethylthiocarbonylamino)-phenyl]-ester.

31. A compound as defined in claim 1, which is α-Cyanobenzyl-N-allyl-carbaminic acid-[3-allyloxycarbonylamino)-phenyl]-ester.

32. A compound as defined in claim 1, which is N-(α-Cyanobenzyl)-N-allylcarbaminic acid-[3-(2-propinyloxycarbonylamino)-phenyl]-ester.

33. A compound as defined in claim 1, which is N-(α-Cyanobenzyl)-N-ethyl-carbaminic acid-[3-(2-propinyloxycarbonylamino)-phenyl]-ester.

34. A compound as defined in claim 1, which is N-(α-Cyano-4-methylbenzyl)-N-ethyl-carbaminic acid-[3-(methoxycarbonylamino)-phenyl]-ester.

35. A compound as defined in claim 1, which is N-(α-Cyano-4-methylbenzyl)-N-ethyl-carbaminic acid-[3-(ethoxycarbonylamino)-phenyl]-ester.

36. A compound as defined in claim 1, which is N-(α-Cyano-4-methylbenzyl)-N-ethyl-carbaminic acid-[3-(ethylthiocarbonylamino)-phenyl]-ester.

37. A compound as defined in claim 1, which is N-(α-Cyano-4-methylbenzyl)-4-ethyl-carbaminic acid-[3-(1-methylethoxycarbonylamino)-phenyl]-ester.

38. A compound as defined in claim 1, which is N-(α-Cyano-4-methylbenzyl)-N-ethyl-carbaminic acid-[3-(allyloxycarbonylamino)-phenyl]-ester.

39. A compound as defined in claim 1, which is N-(α-Cyano-4-methylbenzyl)-N-ethyl-carbaminic acid-[3-(2-methylpropoxycarbonylamino)-phenyl]-ester.

40. A compound as defined in claim 1, which is N-(α-Cyano-4-methylbenzyl)-N-ethyl-carbaminic acid-[3-(2-propinyloxycarbonylamino)-phenyl]-ester.

41. A compound as defined in claim 1, which is N-(α-Cyano-4-methylbenzyl)-N-ethyl-carbaminic acid-[3-(2-propinyloxycarbonylamino)-phenyl-ester.

42. A compound as defined in claim 1, which is N-(α-Cyano-3-methylbenzyl)-N-ethyl-carbaminic acid-[3-(ethoxycarbonylamino)-phenyl]-ester.

43. A compound as defined in claim 1, which is N-(α-Cyano-3-methylbenzyl)-N-ethyl-carbaminic acid-[3-(2-propinyloxycarbonylamino)-phenyl]-ester.

44. A compound as defined in claim 1, which is N-(α-Cyanobenzyl)-N-methyl-carbaminic acid-[3-(1-methylethoxycarbonylamino)-phenyl]-ester.

45. A compound as defined in claim 1, which is N-(α-Cyano-3-methylbenzyl)-N-ethylcarbaminic acid-[3-(allyloxycarbonylamino)-phenyl]-ester.

46. A compound as defined in claim 1, which is N-(α-Cyano-3-methylbenzyl)-N-ethylcarbaminic acid-[3-ethylthiocarbonylamino)-phenyl]-ester.

47. A compound as defined in claim 1, which is N-(α-Cyano-3-methylbenzyl)-N-ethyl-carbaminic acid-[3-(1-methylethoxycarbonylamino)-phenyl]-ester.

48. A compound as defined in claim 1, which is N-(α-Cyano-3-methylbenzyl)-N-ethyl-carbaminic acid-[3-(2-methylpropoxycarbonylamino)-phenyl]-ester.

49. A compound as defined in claim 1, which is N-(α-Cyanobenzyl)-N-methyl-carbaminic acid-[3-(2-propinyloxycarbonylamino)-phenyl]-ester.

50. A compound as defined in claim 1, which is N-(α-Cyanobenzyl)-N-methyl-carbaminic acid-[3-methylpropoxycarbonylamino)-phenyl]-ester.

51. A compound as defined in claim 1, which is N-(α-Cyanobenzyl)-N-ethyl-carbaminic acid-[3-(1-methylethoxycarbonylamino)-phenyl]-ester.

52. A compound as defined in claim 1, which is N-(α-Cyano-4-methoxybenzyl)-N-ethyl-carbaminic acid-[3-(ethoxycarbonylamino)-phenyl]-ester.

53. A compound as defined in claim 1, which is N-(α-Cyano-4-methoxybenzyl)-N-ethyl-carbaminic acid-[3-(ethylthiocarbonylamino)-phenyl]-ester.

54. A compound as defined in claim 1, which is N-(α-Cyano-4-methoxybenzyl)-N-ethyl-carbaminic acid-[3-(1-methylethoxycarbonylamino)-phenyl]-ester.

55. A compound as defined in claim 1, which is N-(α-Cyano-4-methoxybenzyl)-N-ethyl-carbaminic acid-[3-(2-methylpropoxycarbonylamino)-phenyl]-ester.

56. A compound as defined in claim 1, which is N-(α-Cyano-4-methoxybenzyl)-N-ethyl-carbaminic acid-[3-(2-propinyloxycarbonylamino)-phenyl]-ester.

57. A compound as defined in claim 1, which is N-(α-Cyano-4-methoxybenzyl)-N-ethyl-carbaminic acid-[3-(methylthiocarbonylamino)-phenyl]-ester.

58. A compound as defined in claim 1, which is N-(α-Cyano-4-methoxybenzyl)-N-ethyl-carbaminic acid-[3-(methylthiocarbonylamino)-phenyl]-ester.

59. A compound as defined in claim 1, which is N-(α-Cyano-4-chlorobenzyl)-N-ethyl-carbaminic acid-[3-(methoxycarbonylamino)-phenyl]-ester.

60. A compound as defined in claim 1, which is N-(α-Cyano-4-chlorobenzyl)-N-ethyl-carbaminic acid-[3-(methylthiocarbonylamino)-phenyl]-ester.

61. A compound as defined in claim 1, which is N-(α-Cyano-4-chlorobenzyl)-N-ethyl-carbaminic acid-[3-(ethoxycarbonylamino)-phenyl]-ester.

62. A compound as defined in claim 1, which is N-(α-Cyano-4-chlorobenzyl)-N-ethyl-carbaminic acid-[3-(allyloxycarbonylamino)-phenyl]-ester.

63. A compound as defined in claim 1, which is N-(α-Cyano-4-chlorobenzyl)-N-ethyl-carbaminic acid-[3-(ethylthiocarbonylamino)-phenyl]-ester.

64. A compound as defined in claim 1, which is N-(α-Cyano-4-chlorobenzyl)-N-methyl-carbaminic acid-[3-(methoxycarbonylamino)-phenyl]-ester.

65. A compound as defined in claim 1, which is N-(α-Cyano-benzyl)-N-ethyl-carbaminic acid-[3-(methoxycarbonylamino)-phenyl]-ester.

66. A compound as defined in claim 1, which is N-(α-Cyano-benzyl)-N-ethyl-carbaminic acid-[3-(1-methylpropoxycarbonylamino)-phenyl]-ester.

67. A compound as defined in claim 1, which is N-(α-Cyano-benzyl)-N-allylcarbaminic acid-[3-(1-methylethoxycarbonylamino)-phenyl]-ester.

68. A compound as defined in claim 1, which is N-(α-Cyano-benzyl)-N-allyl-carbaminic acid-[3-(2-methylpropoxycarbonylamino)-phenyl]-ester.

69. A compound as defined in claim 1, which is N-(α-Cyano-3,4-dichlorobenzyl)-N-ethyl-carbaminic acid-[3-(2-methylpropoxycarbonylamino)-phenyl]-ester.

70. A compound as defined in claim 1, which is N-(α-Cyano-3-chloro-benzyl)-N-ethyl-carbaminic acid-[3-(2-methylpropoxycarbonylamino)-phenyl]-ester.

71. A compound as defined in claim 1, which is N-(α-Cyano-cyclohexylmethyl)-N-methyl-carbaminic acid-[3-(methoxycarbonylamino)-phenyl]-ester.

72. A compound as defined in claim 1, which is N-(α-Cyano-cyclohexylmethyl)-N-methyl-carbaminic acid-[3-(ethylthiocarbonylamino)-phenyl]-ester.

73. A compound as defined in claim 1, which is N-(α-Cyano-cyclohexylmethyl)-N-methylcarbaminic acid-[3-(2-methylpropoxycarbonylamino)-phenyl]-ester.

74. A compound as defined in claim 1, which is N-(α-Cyano-3-methoxybenzyl)-N-methyl-carbaminic acid-[3-(methylthiocarbonylamino)-phenyl]-ester.

75. A compound as defined in claim 1, which is N-(α-Cyano-3-methoxybenzyl)-N-methylcarbaminic acid-[3-(allyloxycarbonylamino)-phenyl]-ester.

76. A compound as defined in claim 1, which is N-(α-Cyano-3-methoxybenzyl)-N-methylcarbaminic acid-[3-(2-propinyloxycarbonylamino)-phenyl]-ester.

77. A compound as defined in claim 1, which is N-(α-Cyano-3-methoxybenzyl)-N-methylcarbanilic acid-[3-(2-methylpropoxycarbonylamino)-phenyl]-ester.

78. A compound as defined in claim 1, which is N-(1-Cyano-2-phenyl-ethyl)-N-methylcarbaminic acid-[3-(2-propinyloxycarbonylamino)-phenyl]-ester.

79. A compound as defined in claim 1, which is N-(α-Cyano-3,4-dichlorobenzyl)-N-ethyl-carbaminic acid-[3-(methoxycarbonylamino)-phenyl]-ester.

80. A compound as defined in claim 1, which is N-(α-Cyano-3-chlorobenzyl)-N-ethyl-carbaminic acid-[3-(methoxycarbonylamino)-phenyl]-ester.

81. A compound as defined in claim 1, which is N-(α-Cyano-3-methoxybenzyl)-N-methylcarbaminic acid-[3-(methoxycarbonylamino)-phenyl]-ester.

82. A compound as defined in claim 1, which is N-(1-Cyano-2-phenylethyl)-N-methylcarbaminic acid-[3-(methoxycarbonylamino)-phenyl]-ester.

83. A compound as defined in claim 1, which is N-(α-Cyanobenzyl)-N-ethylcarbaminic acid-[3-(4-chloro-2-butinyloxycarbonylamino)-phenyl]-ester.

84. A compound as defined in claim 1, which is N-(1-Cyano-2-phenyl-ethyl)-N-methyl-carbaminic acid-[3-(allyloxycarbonylamino)-phenyl]-ester.

85. A compound as defined in claim 1, which is N-(α-Cyano-2,6-dichlorobenzyl)-N-methylcarbaminic acid-[3-(methoxycarbonylamino)-phenyl]-ester.

86. A compound as defined in claim 1, which is N-(α-Cyano-2,6-dichlorobenzyl)-N-methylcarbaminic acid-[3-(methylthiocarbonylamino)-phenyl]-ester.

87. A compound as defined in claim 1, which is N-(α-Cyano-2,6-dichlorobenzyl)-N-methylcarbaminic acid-[3-(2-propinyloxycarbonylamino)-phenyl]-ester.

88. A compound as defined in claim 1, which is N-(1-Cyano-2-phenyl-ethyl)-N-methylcarbaminic acid-[3-(methylthiocarbonylamino)-phenyl]-ester.

89. A compound as defined in claim 1, which is N-(α-Cyano-2,6-dichlorobenzyl)-N-methylcarbaminic acid-[3-(allyloxycarbonylamino)-phenyl]-ester.

90. A compound as defined in claim 1, which is N-(α-Cyano-2,4-dichlorobenzyl)-N-methylcarbaminic acid-[3-(methoxycarbonylamino)-phenyl]-ester.

91. A compound as defined in claim 1, which is N-(α-Cyano-2,4-dichlorobenzyl)-N-methylcarbaminic acid-[3-(methylthiocarbonylamino)-phenyl]-ester.

92. A compound as defined in claim 1, which is N-(α-Cyano-2,4-dichlorobenzyl)-N-methyl-carbaminic acid-[3-allyloxycarbonylamino)-phenyl]-ester.

93. A compound as defined in claim 1, which is N-(α-Cyano-2,4-dichlorobenzyl)-N-methylcarbaminic acid-[3-(2-propinyloxycarbonylamino)-phenyl]-ester.

94. A compound as defined in claim 1, which is N-(α-Cyano-3-chlorobenzyl)-N-ethylcarbaminic acid-[3-(allyloxycarbonylamino)-phenyl]-ester.

95. A compound as defined in claim 1, which is N-(α-Cyano-3-chlorobenzyl)-N-ethylcarbaminic acid-[3-(2-propinyloxycarbonylamino)-phenyl]-ester.

96. A compound as defined in claim 1, which is N-(α-Cyano-3-chlorobenzyl)-N-ethylcarbaminic acid-[3-(methylthiocarbonylamino)-phenyl]-ester.

97. A compound as defined in claim 1, which is N-(1-Cyano-2-phenylpropyl)-N-methylcarbaminic acid-[3-(ethoxycarbonylamino)-phenyl]-ester.

98. A compound as defined in claim 1, which is N-(1-Cyano-2-phenylpropyl)-N-methyl-carbaminic acid-[3-(methylthiocarbonylamino)-phenyl]-ester.

99. A compound as defined in claim 1, which is N-(α-Cyano-3-chlorobenzyl)-N-ethylcarbaminic acid-3-(ethoxycarbonylamino)-phenylester.

100. A compound as defined in claim 1, which is N-(α-Cyano-3,4-dichlorobenzyl)-N-methylcarbaminic acid-3-(methoxycarbonylamino)-phenylester.

101. A compound as defined in claim 1, which is N-(α-Cyano-3,4-dichlorobenzyl)-N-methylcarbaminic acid-3-(ethoxycarbonylamino)-phenylester.

102. A compound as defined in claim 1, which is N-(α-Cyano-3,4-dichlorobenzyl)-N-methylcarbaminic acid-3-(methylthiocarbonylamino)-phenylester.

103. A compound as defined in claim 1, which is N-(α-Cyano-3,4-dichlorobenzyl)-N-methylcarbaminic acid-3-(allyloxycarbonylamino)-phenylester.

104. A compound as defined in claim 1, which is N-(α-Cyano-3,4-dichlorobenzyl)-N-methylcarbaminic acid-3-(allyloxycarbonylamino)-phenylester.

105. A compound as defined in claim 1, which is N-(1-Cyano-2-phenylpropyl)-N-methylcarbaminic acid-3-(2-propinyloxycarbonylamino)-phenylester.

106. A compound as defined in claim 1, which is N-(1-Cyano-2-phenylpropyl)-N-methylcarbaminic acid-3-(allyloxycarbonylamino)-phenylester.

107. A compound as defined in claim 1, which is N-(1-Cyano-2-phenylpropyl)-N-methylcarbaminic acid-3-(ethylthiocarbonylamino)-phenylester.

108. A compound as defined in claim 1, which is N-(α-Cyano-3-chlorobenzyl)-N-methylcarbaminic acid-3-(methoxycarbonylamino)-phenylester.

109. A selective herbicidal composition comprising an effective amount of at least one compound as defined in claim 1 as active agent in admixture with a carrier material.

110. A composition as defined in claim 1, comprising between about 10 and 80 weight-% active agent.

* * * * *